Figure 1:
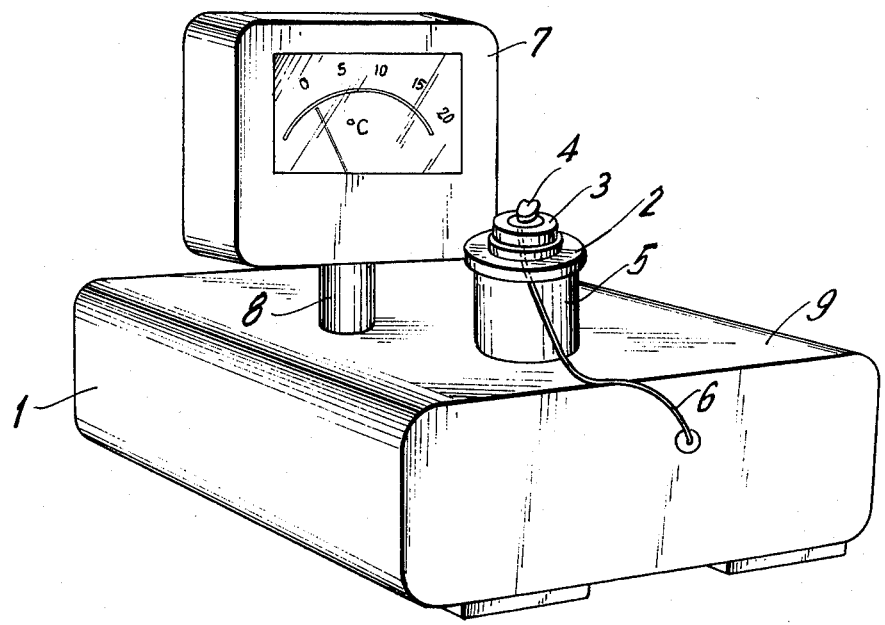

United States Patent [19]
Henning

[11] 3,950,852
[45] Apr. 20, 1976

[54] TRAINING INSTRUMENT FOR DENTAL PROCEDURES

[76] Inventor: Gerd F. Henning, D-785 Lorrach 6, Taubenacker 7, Germany

[22] Filed: Apr. 18, 1975

[21] Appl. No.: 569,224

[52] U.S. Cl. .................................................. 32/71
[51] Int. Cl.² ..................................... A61C 19/00
[58] Field of Search .......... 128/2 H; 73/343; 32/71, 32/40 R

[56] References Cited
UNITED STATES PATENTS

| | | | |
|---|---|---|---|
| 2,812,578 | 11/1957 | Weldonhamer | 32/71 |
| 3,054,397 | 9/1962 | Benzinger | 73/343 R |

*Primary Examiner*—Robert Peshock
*Attorney, Agent, or Firm*—Friedman & Goodman

[57] ABSTRACT

A training device for dental purposes is provided with elements for measuring thermal effects in dental treatment, as in the preparation of teeth. The device includes a base member upon which a tooth is to be treated. The tooth is embedded in a supporting receptacle fabricated from a synthetic resin which exhibits a thermal capacity equal or similar to that of a dentin. The receptacle is mounted on a removable work head member which is disposed on the base member. A thermal-element is apically positioned in a tooth in contact with its pulp wall. The thermal-element is associated with an amplifier for connection to a temperature indicator and/or a registering instrument. Preferably, the temperature indicator is rotatably mounted on the base member. Additionally, the work head member is rotatably mounted, such as by a ball joint removable connection.

8 Claims, 2 Drawing Figures

U.S. Patent  April 20, 1976  3,950,852

TRAINING INSTRUMENT FOR DENTAL PROCEDURES

This invention relates to a training instrument for dental purposes wherein means are provided for measuring thermal effects during dental procedures, such as in the preparation of teeth.

In the practice of dental procedures, especially in the preparation for fillings, crowns, etc., numerous training or types of instruments are available. Literature in this art is in agreement to the effect that the concept of the maintenance of the vitality of the pulp is the most important rule to be followed. According to the pertinent literature, the development of a high pulp temperature, during treatment is detrimental.

The object of this invention is to develop a device for permitting methods of treatment, execution and adaptability to be studied with the widest variety of expedients. In order that the results of the treatment procedures, carried out by a dental device, provide the best possible approximation of actual in vivo conditions, numerous factors must be taken into consideration.

This invention solves the above problem in a novel manner in that the present device comprises a base or pedestal member upon which a tooth is supported, being disposed in a freely mounted work head. The tooth is embedded in a receptacle. A thermo-element is introduced apically into the tooth so that it contacts the pulp wall. The base or pedestal member is provided with an amplifier interconnected with the thermo-element and a temperature indicating and/or registering instrument.

The advantages of this novel solution are apparent. The temperature in the pulp cavity is not falsified by means of the thermo-element which is employed. The heat capactiy of the thermo-element is substantially lower than that of the dentin. The response time of the temperature measuring arrangement is extremely small, as for example about 0.05 seconds. The thermo-element may be properly located in the pulp cavity since a nonmetallic character of the mounting permits it to be controlled by X-ray means.

In order to reproduce in vivo conditions as closely as possible, extracted teeth which have been stored in an isotonic salt solution are utilized. During the treatment of a natural tooth, some of the heat generated is conducted through the vital pulp and tooth to its surrounding tooth supporting tissue. In order to simulate this effect, and to avoid heat vaporization in the present invention, the extracted tooth is embedded in a synthetic resin.

For this purpose, a methacrylate synthetic resin has proven to be especially suitable. The necessary quantity of synthetic resin can be calculated through equalization of the calorific values. In the employment of the device of this invention, the measured temperature is compared with the room temperature. One can thus proceed so that the measured values can be carried over quantitively to the body temperature. In vivo, the absolute temperatures according to the body/room temperature difference will be lower than by tests conducted according to the invention. The measured relative temperature elevation is directly comparable.

The above effect can be artificially simulated, in that the water and compressed air temperatures are lowered to the body/room temperature difference by experimentation with the present device. With the inventive device, it is possible, not only to provide an expedient for self control for practising dentists and students, but also to determine optimal treatment parameters. In particular, it is possible to carry out tests with reference to cooling media and instruments.

Figure 2:
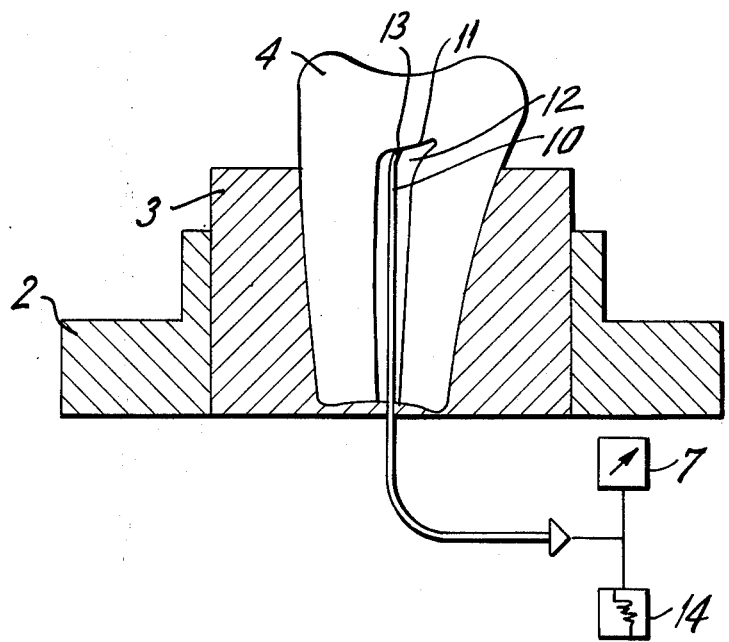

An embodiment of the invention is schematically illustrated in the accompanying drawings in which:

FIG. 1 is a perspective view of a device according to the present invention; and FIG. 2 is a cross-section of a measuring head in accordance with FIG. 1.

As may be seen from the drawings, the inventive device comprises a base 1 and a work head 2 which carries a tooth receptacle 3, preferably a ring of synthetic resin which exhibits a thermal capability equal or similar to that of dentin, such as a methacrylate synthetic resin. The work head is rotatably and/or swivelably mounted on a type of ball joint, so that it may be disposed in any desired orientation. The support for the ball joint is additionally rotatably and adjustably secured to the base 1.

The thermo-element leads 6 are connected from the pulp area to a recorder 14 and from this through an equalizing circuit to an amplifier disposed under the base, which is interconnected with a temperature indicating device 7. The recorder 14 may be an XY recorder, which acts as a registering device. The temperature indicating device 7 is preferably graduated in degrees Celcius and, similarly to the work head, is rotatably mounted by post 8 on the base.

By reason of the rotatability of the temperature indicating device, it is possible in working with the inventive device, for the operator to exercise indirect control during the operation without being influenced in his works by the temperature indicator. This can occur in the simplest manner as a consequence of turning the scale of the indicating instrument away from the operator. He can subsequently control his treatment from the recorded temperature curve of the registering device 14. A collecting dish, for the cooling medium such as cooling water, is provided on the surface 9 of the base 1 facing the work head 2.

As may be understood from FIG. 2, the thermo-element 10, preferably formed of nickel chrome/nickel wire with a glass or steel sheath and a wire diameter of 0.1mm, is apically positioned in a tooth 4 which is embedded in the receptacle 3, and touches the wall 11 of pulp cavity 12 with its hot solder joint 13. The work head 2 is fabricated from a non-metallic material, and is supported above the base 1 by a support member which may be surrounded by a sheet metal cover 5. The work head 2 is removable from the base so it may be easily x-rayed. Obviously, the work head can be provided with a plug-type connector whereby the ends of the thermo-element wires 6 are in one of the male-female connectors while the equalizing circuit lead ends are in the other electrical connector.

In place of a thermo-element, a suitable fast response semi-conductor (NTC-resistance) may be employed. It is understood that it is possible to provide other indicating and control instruments on the base. The inventive device permits for the first time, the investigation of different parameters of treatment such as instrument pressure, rotational speed, cooling media etc. by training means. The following influences may be particularly investigated: (a) dental instruments such as steel, hand metal and diamond drill tools, (b) various rotational speeds in the range of 40,000 to 350,000 RPM, being micro-motor or turbine driven, and (c) various cooling methods such as air cooling, cooling mixture sprays such as in liquid/gas form, and hand pieces provided with added cooling.

What is claimed is:

1. A training device for dental procedures used in measuring thermal effects of dental treatment as in preparation of teeth, said device comprising a base member upon which the tooth is to be treated, a work head member being freely accessibly, removably mounted on said base member, the tooth being embedded in a supporting receptacle disposed on said work head member, thermo-element means being apically positioned in the tooth in contact with pulp wall of the tooth to obtain temperature thereof, said thermo-element means being connected to at least one of a temperature indicator and registering instrument for visually indicating the temperature.

2. A training device according to claim 1, wherein said receptacle is releasably held in said work head member.

3. A training device according to claim 1, wherein said receptacle for the tooth is fabricated from a synthetic resin, said resin having thermal capability approximately equal to that of dentin.

4. A training device according to claim 3, wherein said receptacle for the tooth is fabricated from a methacrylate synthetic resin.

5. A training device according to claim 1, including means for said temperature indicator to be rotatably mounted on said base member.

6. A training device according to claim 1, wherein said temperature indicator is mounted on said base member.

7. A training device according to claim 1, wherein a surface of said base member facing said work head member is planar to carry a cooling media collecting dish.

8. A training device according to claim 1, wherein said work head member is provided with means for rotatably and swivelably mounting thereof relative to said base member.

* * * * *